(12) United States Patent
Buchholz et al.

(10) Patent No.: US 7,348,037 B2
(45) Date of Patent: Mar. 25, 2008

(54) SULFUR-CONTAINING ANIMAL-FEED ADDITIVES

(75) Inventors: Michael Buchholz, Bielefeld (DE); Michael Binder, Hasselroth-Niedermittlau (DE); Thomas Hermann, Bielefeld (DE); Walter Pfefferle, Halle (DE); Georg Thierbach, Bielefeld (DE)

(73) Assignee: Evonik Degussa GmbH, Duesseldorf (DE)

( * ) Notice: Subject to any disclaimer, the term of this patent is extended or adjusted under 35 U.S.C. 154(b) by 707 days.

(21) Appl. No.: 10/637,600

(22) Filed: Aug. 11, 2003

(65) Prior Publication Data

US 2005/0271768 A1 Dec. 8, 2005

Related U.S. Application Data

(60) Provisional application No. 60/404,126, filed on Aug. 19, 2002.

(30) Foreign Application Priority Data

Aug. 16, 2002 (DE) ................. 102 37 479

(51) Int. Cl.
*A23K 1/00* (2006.01)
*A23K 1/18* (2006.01)

(52) U.S. Cl. .............. 426/656; 426/2; 426/61; 426/807

(58) Field of Classification Search .............. 426/2, 426/61, 656, 807
See application file for complete search history.

(56) References Cited

U.S. PATENT DOCUMENTS

| 5,431,933 | A | * | 7/1995 | Binder et al. | ............... 426/60 |
| 5,622,710 | A | * | 4/1997 | Binder et al. | ............... 424/438 |
| 5,972,663 | A | * | 10/1999 | Winterhalter et al. | ....... 435/113 |
| 6,218,168 | B1 | * | 4/2001 | Leinfelder et al. | ....... 435/252.3 |
| 6,238,728 | B1 | * | 5/2001 | Ishiguri et al. | ............. 426/656 |
| 6,465,025 | B2 | * | 10/2002 | Binder et al. | ............... 426/2 |

FOREIGN PATENT DOCUMENTS

| EP | 0 885 962 | 12/1998 |
| WO | WO 97/15673 | 5/1997 |
| WO | WO 01/27307 | 4/2001 |
| WO | WO 02/29029 | 4/2002 |
| WO | WO 02/061106 | 8/2002 |

OTHER PUBLICATIONS

Nutrient Requirements of Dairy Cattle, National Research Council, Sixth Revised Edition, 1989, pp. 28-29.*
Baker, "Utilization of Precursors for L-Amino Acids" (pp. 37-61).

\* cited by examiner

*Primary Examiner*—C. Sayala
(74) *Attorney, Agent, or Firm*—Oblon, Spivak, McClelland, Maier & Neustadt, P.C.

(57) ABSTRACT

The invention relates to sulfur-containing animal-feed additives produced from fermentation liquors, and to processes for their production.

10 Claims, 1 Drawing Sheet

```
                        SEQUENCE LISTING

<160> NUMBER OF SEQ ID NOS: 5

<210> SEQ ID NO 1
<211> LENGTH: 50
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
gatctaccat ggaaaggagg acaaccatga aattcagagg cggtagaatg            50

<210> SEQ ID NO 2
<211> LENGTH: 37
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
gatctagaat tcgtagtttg ttctggcccc gacatct                          37

<210> SEQ ID NO 3
<211> LENGTH: 33
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
gatctggatc cgccgacatc ataacggttc tgg                              33

<210> SEQ ID NO 4
<211> LENGTH: 40
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
gatctagaat tcaagcttgg ctaccgcaat acgaagaag                        40
```

```
<210> SEQ ID NO 5
<211> LENGTH: 34
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
gatctaggat ccggcacgat cacaggacat taga                                34
```

SULFUR-CONTAINING ANIMAL-FEED ADDITIVES

FIELD OF THE INVENTION

The invention relates to sulfur-containing animal-feed additives produced from fermentation liquors.

BACKGROUND OF THE INVENTION

L-Cysteine and its derivatives are used in the pharmaceuticals sector, in cosmetics and in the foodstuffs industry. For those applications, L-cysteine is typically produced in pure form.

L-Cysteine is traditionally obtained by extraction from materials containing keratin, such as, for example, hair, bristles and feathers, or by enzymatic reaction of precursors.

For some years, L-cysteine has also been produced by fermentation using microorganisms that overproduce L-cysteine. WO 97/15673, EP-A-0885962 and WO 01/27307 describe processes for the production of O-acetylserine, L-cysteine or L-cysteine derivatives and related products using E. coli microorganisms.

WO 97/15673 relates to a process for the production of O-acetylserine, L-cysteine and sulfur-containing compounds derived therefrom, using feed-back resistant serine-acetyl transferases. Such serine-acetyl transferases have reduced sensitivity to the inhibitor L-cysteine in comparison with the wild-type enzyme.

EP-A-0885962 describes microorganisms containing at least one overexpressed gene coding for a protein that directly for the elimination from the cell of antibiotics or other substances toxic for the microorganism, and a process for the production by fermentation of L-cysteine, L-cystine, N-acetyl-serine or thiazolidine derivatives using such microorganisms.

WO 01/27307 describes a process for the production of L-cysteine or L-cysteine derivatives by means of fermentation of microorganisms, as well as microorganisms suitable for the process. Such microorganisms possess increased activity of the transcription regulator CysB, the CysB activity having a regulation pattern typical for a wild-type CysB.

L-Cysteine occupies a key position in the metabolism of sulfur and is used in the synthesis of proteins, glutathione, biotin, methionine and other sulfur-containing metabolites. However, it is also known that L-cysteine has reducing properties and accordingly has various problems in handling, such as, for example, stability.

OBJECT OF THE INVENTION

The object of the invention is, therefore, to provide novel sulfur-containing animal-feed additives. An additional object of this invention is to provide a process for the production of such sulfur-containing animal-feed additives.

DESCRIPTION OF THE INVENTION

The invention provides animal-feed additives based on fermentation liquor, characterized in that they contain at least
 a) one or more cysteine compounds selected from the group L-cysteine, L-cystine and thiazolidines, including their salts, and
 b) from 2% to 100% of the further non-cellular ingredients of the fermentation liquor.

The invention also provides processes for the production of the animal-feed additives according to the invention.

Cysteine compounds are understood as being L-cysteine, the dimer L-cystine and thiazolidines, including their salts. The content of cysteine compounds in the feed additives according to the invention is from 1 to 98 wt. % (percent by weight).

Thiazolidines and the corresponding hemithioketals are understood as being the reaction products of L-cysteine with compounds containing a carbonyl group, that is to say ketones and aldehydes such as, for example, pyruvic acid (pyruvate) and glyoxylic acid (glyoxylate). The condensation of L-cysteine with pyruvic acid yields methyl-thiazolidine-2,4-dicarboxylic acid, and condensation with glyoxylic acid yields thiazolidine-2,4-dicarboxylic acid or the corresponding hemithioketal. The thiazolidines also include, inter alia, 2-carboxymethyl-thiazolidine-2,4-dicarboxylic acid and 2-carboxyethyl-thiazolidine-2,4-dicarboxylic acid or the corresponding hemithioketal.

The cysteine compounds are optionally in the form of their salts, the salts of the cysteine compounds being one or more salts selected from the group of the sodium, potassium, ammonium, magnesium or calcium salts.

A fermentation liquor is understood as being a fermentation medium in which a microorganism has been cultivated for a certain time and at a certain temperature. The fermentation medium or culture medium contains all the substances or components that ensure multiplication of the microorganism and formation of the desired chemical compounds, in the case of the present invention one or more compounds selected from the group L-cysteine, L-cystine and thiazolidines.

When the fermentation is complete, the resulting fermentation liquor contains a) the biomass of the microorganism, the biomass being formed as a result of the multiplication of the cells of the microorganism, b) the chemical compounds formed in the course of the fermentation, and c) the unused constituents of the fermentation medium or fermentation media used.

The chemical compounds that are formed include the products that are desired directly, in the case of the present invention one or more compounds selected from the group L-cysteine, L-cystine and thiazolidines, and secondary products. The secondary products are optionally also desired.

The expression "further non-cellular ingredients of the fermentation liquor" is understood as meaning, according to the invention, all the constituents of the fermentation liquor minus the biomass and minus the desired products, in the case of the present invention one or more compounds selected from the group L-cysteine, L-cystine and thiazolidines. The addition "further" in the expression "further non-cellular ingredients of the fermentation liquor" has been used because L-cysteine, L-cystine and thiazolidines are by their nature also non-cellular ingredients of the fermentation liquor. In other words, the ingredients in question are the secondary products that are formed and the unused constituents of the fermentation media.

The following mathematical symbols are used hereinbelow: > means greater or more than; $\geq$ means greater than or equal to; < means smaller or less than; and $\leq$ means less than or equal to.

The further non-cellular ingredients of the fermentation liquor remain in the animal-feed additives according to the invention, as desired, to the extent of from 2% to 100%, from 3% to 100%, from 4% to 100%, from 5% to 100%, from 10% to 100%, from 20% to 100%, from 30% to 100%, from 40% to 100%, from 50% to 100%, from 60% to 100%, from 70% to 100%, from 80% to 100% or from 90% to 100%, preferably ≧50%, ≧60%, ≧70%, ≧80%, ≧90% or ≧95%. They may optionally also be present in their entirety (100%).

The further non-cellular ingredients of the fermentation liquor include one or more of the secondary products that are produced or generated in the fermentation of L-cysteine-forming microorganisms in addition to one or more cysteine compounds selected from the group L-cysteine, L-cystine and thiazolidines. Those secondary products include, for example, sugars, such as trehalose.

Those secondary products additionally include organic acids carrying from one to three carboxyl groups, such as, for example, acetic acid, lactic acid, citric acid, malic acid or fumaric acid.

Those secondary products also include L-amino acids selected from the group L-lysine, L-valine, L-threonine, L-alanine, L-tryptophan, L-serine, glycine, and the sulfur-containing amino acid L-methionine. They also include amino acid derivatives from the group of the N- and O-acetylated amino acids, for example N-acetyl-serine and O-acetyl-serine.

Those secondary products also include vitamins selected from the group the sulfur-containing vitamin B1 (thiamin), vitamin B2 (riboflavin), vitamin B5 (pantothenic acid), vitamin B6 (pyridoxal), vitamin B12 (cyanocobalamin), the sulfur-containing vitamin H (biotin), vitamin H (tocopherol) and nicotinic acid or nicotinic acid amide.

Those secondary products likewise include sulfur-containing metabolic products such as, for example, glutathione, cystathionine, liponic acid and coenzyme A.

The further non-cellular ingredients of the fermentation liquor also include residues of the inorganic and organic components of the fermentation media used.

The inorganic components are, for example, calcium and magnesium in the form of their cations, phosphorus in the form of phosphate, and sulfur in the form of sulfate.

The organic components are, for example, sugars, such as, for example, glucose, fructose or isomaltose, vitamins, such as, for example, biotin or thiamin, and organic acids, such as, for example, citric acid (citrate). The mentioned components of the fermentation medium may also be constituents from complex substance mixtures, such as extracts, for example yeast extract, peptones and hydrolysates, or from other additives, such as corn steep liquor (CSL) or molasses.

The chemical compounds that make up the further non-cellular ingredients of the fermentation liquor are desirable if they improve the nutritional effectiveness of the animal-feed additive.

The mentioned chemical compounds, and also other compounds which have an advantageous effect on the production of the animal-feed additives according to the invention, such as, for example, ascorbic acid (vitamin C), tocopherol (vitamin E), soybean oil or formic acid or salts thereof, are optionally added during the working-up process or during the fermentation.

In order to achieve the desired content in the animal-feed additive, one or more cysteine compounds selected from the group L-cysteine, L-cystine and thiazolidines, or preparations or mixtures containing them, are optionally added, as required, during the working-up process or towards or at the end of the fermentation.

A further aspect of this invention is an animal-feed additive which contains 0% to 100% of the biomass, formed during the fermentation, of the microorganism.

In that respect, the animal-feed additives according to the invention can be divided into three groups: a) animal-feed additives that are free of biomass, in which the biomass has been separated off completely (100%), b) animal-feed additives that are low in biomass, which contain at most half (≦50%), or less than half or alternatively only insignificant residues of the biomass formed, and c) animal-feed additives that are rich in biomass, which contain the predominant part (>50%) or all of the biomass formed.

The animal-feed additives according to the invention of group b) contain >0% to ≦50%, >0% to ≦40%, >0% to ≦30%, >0% to ≦20%, >0% to ≦10%, >0% to ≦5%, >0% to ≦1% or >0% to ≦0.1% of the biomass formed.

The animal-feed additives according to the invention of group c) can contain >50% to 100%, >60% to 100%, >70% to 100%, >80% to 100%, >90% to 100% or >95% to 100% of the biomass formed.

A further aspect of this invention concerns storable liquid or solid animal-feed additives. The term "storable" means that the liquid or solid animal-feed additives according to the invention can be stored for at least 2 months without there being any substantial loss (<5%) of cysteine compounds.

The invention further provides a process for the production of animal-feed additives, characterized in that it comprises
   a) separating the biomass completely (100%) from fermentation liquors containing cysteine compounds selected from the group L-cysteine, L-cystine and thiazolidines, and
   b) optionally concentrating the mixture so obtained by removal of water.

In order to produce a further liquid form of the animal-feed additive according to the invention, namely a liquid form low in biomass, virtually all or at least the predominant part (≧50% to <100%) of the biomass is removed from the resulting fermentation liquor by separation methods such as, for example, centrifugation, filtration, decantation, flocculation or a combination thereof.

The liquor low in biomass can also be obtained by removing the biomass completely from a larger portion (≧50% to <100%) of a given, biomass-containing fermentation liquor (100%) and mixing the biomass-free portion so obtained with the remaining smaller, biomass-containing portion (>0% to ≦50%) of the fermentation liquor.

The resulting liquor low in biomass is then optionally thickened or concentrated by known methods, such as, for example, by means of a rotary evaporator, a thin-layer evaporator, a falling film evaporator, by reverse osmosis, or by nanofiltration.

Such low-biomass variants of the liquid forms of the animal-feed additives according to the invention contain >0% to ≦50%, >0% to ≦40%, >0% to ≧30%, >0% to ≦20%, >0% to ≦10%, >0% to ≦5%, >0% to ≦1% or >0% to ≦0.1% of the biomass formed during the fermentation.

In this respect, the invention further provides a process for the production of animal-feed additives that are low in biomass, characterized in that it comprises
   a) separating virtually all or at least the predominant part (≧50% to <100%) of the biomass from fermentation liquors containing cysteine compounds selected from the group L-cysteine, L-cystine and thiazolidines, and
   b) optionally concentrating the mixture so obtained by removal of water.

In order to produce a further liquid form of the animal-feed additive according to the invention, namely a liquid form that is rich in biomass, all or at least the predominant part (>50% to 100%) of the biomass is left in the fermentation liquor. As required, at most a small portion of the biomass is removed from the resulting fermentation liquor by separation methods such as, for example, centrifugation, filtration, decantation, flocculation or a combination thereof.

The liquor rich in biomass can also be obtained by removing the biomass completely from a smaller portion (>0% to <50% or ≧0% to <50%) of a given, biomass-containing fermentation liquor (100%) and mixing the biomass-free portion so obtained with the remaining larger, biomass-containing portion (>50% to <100% or >50% to ≦100%) of the fermentation liquor.

The resulting liquor is then optionally thickened or concentrated by known methods, such as, for example, by means of a rotary evaporator, a thin-layer evaporator, a falling film evaporator, by reverse osmosis, or by nanofiltration.

Such biomass-rich variants of the liquid forms of the animal-feed additives according to the invention contain >50% to 100%, >60% to 100%, >70% to 100%, >80% to 100%, >90% to 100% or >95% to 100% of the biomass formed during the fermentation.

Accordingly, the invention also provides a process for the production of animal-feed additives that are rich in biomass, characterized in that it comprises
 a) leaving all or the predominant part (100% to >50%) of the biomass in fermentation liquors containing cysteine compounds selected from the group L-cysteine, L-cystine and thiazolidines, and
 b) optionally concentrating the mixture so obtained by removal of water.

The biomass is preferably in inactive form, that is to say in a form that is not capable of multiplication. If some or all of the biomass is left in the animal-feed additive, that additive contains the proteins and the further constituents of the microorganism as an additional nutritionally effective component.

The animal-feed additives according to the invention may be in liquid or solid form.

The contents of cysteine compounds in the liquid forms are generally from 1 to 35 wt. %, from 2 to 35 wt. %, from 4 to 35 wt. %, from 6 to 35 wt. %, from 8 to 35 wt. % or from 10 to 35 wt. %. They may be in dissolved or suspended form. The total dry material in the liquid forms of the animal-feed additive is generally from 5 to 60 wt. %.

The total dry material is understood as being the proportion of all the dissolved and suspended substances that remains after removal of water from the sample to be tested (removal of water by drying until a constant weight is achieved).

The content of cysteine compounds in the solid forms of the animal-feed additives is generally from 1 to 98 wt. %, from 2 to 98 wt. %, from 4 to 98 wt. %, from 6 to 98 wt. %, from 8 to 98 wt. %, from 10 to 98 wt. %, from 15 to 98 wt. % or from 20 to 98 wt. %, based on the total dry material of the animal-feed additives. Contents from 1 to 90 wt. %, from 2 to 90 wt. %, from 4 to 90 wt. %, from 6 to 90 wt. %, from 8 to 90 wt. %, from 10 to 90 wt. %, from 15 to 90 wt. % or from 20 to 90 wt. %, or contents from 1 to 80 wt. %, from 2 to 80 wt. %, from 4 to 80 wt. %, from 6 to 80 wt. %, from 8 to 80 wt. %, from 10 to 80 wt. %, from 15 to 80 wt. % or from 20 to 80 wt. %, or contents from 1 to 60 wt. %, from 2 to 60 wt. %, from 4 to 60 wt. %, from 6 to 60 wt. %, from 8 to 60 wt. %, from 10 to 60 wt. %, from 15 to 60 wt. % or from 20 to 60 wt. %, or contents from 1 to 40 wt. %, from 2 to 40 wt. %, from 4 to 40 wt. %, from 6 to 40 wt. %, from 8 to 40 wt. % or from 10 to 40 wt. %, are also possible.

The water content in the solid forms is usually up to 5 wt. %, preferably up to 4 wt. % and particularly preferably less than 2 wt. %.

The thiazolidine content is at least 0.001 wt. % or at least 0.01 wt. % or at least 0.1 wt. % or is at least present in traces. "Traces" is to be understood as meaning amounts of from >0% to 5%, preferably >0 to 0.01 wt. %.

The solid forms are, as required, in the form of spray-dried or lypophilised, finely divided, pourable powders or alternatively in granulated or coarse-grained, largely dust-free, but in any case pourable form.

The term "pourable" means powders that flow unhindered at least from the vessel of a series of glass discharge vessels having discharge openings of different sizes that has the 5 mm (millimeter) opening (Klein, Seifen—Öle—Fette—Wachse 94 (24), 849-858 (1968)).

The term "finely divided" means a powder the predominant portion (>50%) of which has a grain size of from 20 to 200 μm diameter.

The term "coarse-grained" means products the predominant portion (>50%) of which has a grain size of from 200 to 2000 μm diameter.

The term "dust-free" means that the product contains only small proportions (<5%) of grain sizes below 20 μm diameter.

Methods of determining the grain size are described, for example, in the textbook "Teilchengrößenmessung in der Laborpraxis" by R. H. Müller and R. Schuhmann (Wissenschaftliche Verlagsgesellschaft Stuttgart (1996)) or in the textbook "Introduction to Particle Technology" by M. Rhodes (Verlag Wiley & Sons (1998)).

The solid forms of the animal-feed additives according to the invention may also contain an organic or inorganic carrier that is known and conventional in animal-feed processing, such as, for example, silicas, silicates, meals, brans, cereal flours, flours, starches, sugars, etc., or conventional thickeners or binders.

They may also contain film-forming agents, such as, for example, metal carbonates, silicas, silicates, alginates, stearates, starches, rubbers and cellulose ethers, which bring the product into a state in which it is stable to digestion by animal stomachs.

For the preparation of fermentation liquors containing cysteine compounds, it is possible to use Gram-negative bacteria, Gram-positive bacteria, yeasts or fungi that are capable of forming L-cysteine intracellularly or extracellularly in a suitable fermentation medium.

Of the Gram-negative bacteria, special mention may be made of *Escherichia coli*. L-Cysteine-producers of *Escherichia coli* are, for example, the strains described in WO 97/15673
 JM15 transformed with the plasmid pACYC184/cysEIV,
 JM15 transformed with the plasmid pACYC184/cysEV,
 JM15 transformed with the plasmid pACYC184/cysEX,
 JM15 transformed with the plasmid pACYC184/cysEXI,
 JM15 transformed with the plasmid pACYC184/cysEXII,
 JM15 transformed with the plasmid pACYC184/cysEXIV,
 JM15 transformed with the plasmid pACYC184/cysEXV,
 JM15 transformed with the plasmid pACYC184/cysEXVI,
 JM15 transformed with the plasmid pACYC184/cysEXXIII, and
 JM15 transformed with the plasmid pACYC184/cysEDel1255

Further L-cysteine-producers of *Escherichia coli* are, for example, the strains described in EP-A-0885962
 W3110 transformed with the plasmid 100-1-1,
 W3110 transformed with the plasmid pACYC184/cysEIV, W3110 transformed with the plasmid pACYC184/cysEIV-mar, W3110 transformed with the plasmid pACYC184/cysEIV-GAPDH-ORF306, W3110 transformed with the plasmid pACYC184/cysEX, W3110 transformed with the plasmid pACYC184/cysEX-mar, and W3110 transformed with the plasmid pACYC184/cysEX-GAPDH-ORF306.

In WO 01/27307, the following L-cysteine-producing strains of *Escherichia coli* are described:

W3110 transformed with the plasmid pHC30, and

W3110 transformed with the plasmid pHC34.

In Nakamori et al. (Applied and Environmental Microbiology, 1998, 64, 1607-1611), the following L-cysteine-producing strains of *Escherichia coli* are described:

*Escherichia coli* JM39-8 pCEM256A,

*Escherichia coli* JM39-8 pCEM256E,

*Escherichia coli* JM39-8 pCEM256Stop,

*Escherichia coli* JM39-8 pCEM256S, and

*Escherichia coli* JM39 pCEM256D.

In Takagi et al. (FEBS Letters, 1999, 452, 323-327), the following L-cysteine-producing strains of *Escherichia coli* are described:

*Escherichia coli* W3110 pACYC184-LH, and

*Escherichia coli* MC4100 pKP291

In Daβler et al. (Molecular Microbiology, 2000, 36, 1101-1112), the following L-cysteine-producing strain of *Escherichia coli* is described:

W3110 transformed with the plasmid pKP291.

The strains of *Escherichia coli* described by Mino et al. (Bioscience, Biotechnology and Biochemistry, 1999, 63, 168-179) can also be used.

Of the Gram-positive bacteria, mention may be made of *Corynebacterium glutamicum*, for example. L-Cysteine-producers of *Corynebacterium glutamicum* are, inter alia, the strains described in WO 97/15673:

ATCC21851 transformed with the plasmid pWST1-cysEIV,

ATCC21851 transformed with the plasmid pWST1-cysEX,

ATCC21851 transformed with the plasmid pWST1-cysEXI, and

ATCC21851 transformed with the plasmid pWST1-cysEXIV.

It is optionally possible to use microorganisms that convert a chemical precursor to L-cysteine and/or L-cystine.

For example, Yamamoto et al. (Nippon Nogei Kagaku Kaishi, 2000, 74(8), 891-895) describe the enzymatic conversion of DL-2-thiazolidine-4-carboxylic acids to L-cystine with

*Pseudomonas desmolytica* AJ-11071.

Toshikazu et al. (U.S. Pat. No. 6,214,590), for example, describe the conversion of 2-aminothiazolidine-4-carboxylic acid to L-cysteine and L-cystine with

*Pseudomonas ovalis* BS.

For the preparation of fermentation liquors containing one or more cysteine compounds selected from the group L-cysteine, L-cystine and thiazolidines, the L-cysteine-producing microorganisms can be cultivated continuously or discontinuously by the batch process or by the fed batch or repeated fed batch process.

A summary of known cultivation methods is described in the textbook of Chmiel (Bioprozesstechnik 1. Einführung in die Bioverfahrenstechnik (Gustav Fischer Verlag, Stuttgart, 1991)) or in the textbook of Storhas (Bioreaktoren und periphere Einrichtungen (Vieweg Verlag, Braunschweig/Wiesbaden, 1994)).

The culture medium to be used must meet the requirements of the strains in question in a suitable manner. Descriptions of culture media for various microorganisms are contained in the handbook "Manual of Methods for General Bacteriology" of the American Society for Bacteriology (Washington D.C., USA, 1981).

There may be used as the carbon source or substrates sugars and carbohydrates, such as, for example, glucose, saccharose, lactose, fructose, maltose, molasses, starch hydrolysate, starch and cellulose, oils and fats, such as, for example, soybean oil, sunflower oil, groundnut oil and coconut oil, fatty acids, such as, for example, palmitic acid, stearic acid and linoleic acid, alcohols, such as, for example, glycerol and ethanol, and organic acids, such as, for example, acetic acid and lactic acid. Those substances may be used individually or in the form of a mixture.

It is advantageous for the fermentation to be carried out with limited substrate, especially with limited sugar, at least at the end, but especially for at least 30% of the duration of the fermentation. That means that the concentration of usable substrate, especially sugar, in the fermentation medium is maintained at, or reduced to, $\geq 0$ to 3 g/l during that time.

There may be used as the nitrogen source organic nitrogen-containing compounds, such as peptones, yeast extract, meat extract, malt extract, corn steep liquor, soybean flour and urea, or inorganic compounds, such as ammonium sulfate, ammonium chloride, ammonium phosphate, ammonium carbonate and ammonium nitrate. The nitrogen sources may be used individually or in the form of a mixture.

There may be used as the sulfur source organic and inorganic sulfur-containing compounds, such as, for example, sulfides, sulfites, dithionite, thiosulfates and sulfates. The sulfur sources may be used individually or in the form of a mixture.

There may be used as the phosphorus source phosphoric acid, potassium dihydrogen phosphate or dipotassium hydrogen phosphate or the corresponding sodium-containing salts. The culture medium must also contain salts of metals, such as, for example, magnesium sulfate or iron sulfate, which are necessary for growth. Finally, essential growth substances, such as amino acids and vitamins, may be used in addition to the above-mentioned substances. Suitable precursors may also be added to the culture medium. The mentioned substances may be added to the culture in the form of a single batch, or they may be suitably fed in during the cultivation.

In order to control the pH value of the culture, basic compounds, such as sodium hydroxide, potassium hydroxide, ammonia or ammonia water, or acid compounds, such as phosphoric acid or sulfuric acid, are used in a suitable manner. The pH value is generally from pH 6.0 to pH 8.0, preferably from pH 6.5 to pH 7.5. In order to control the development of foam, anti-foams, such as, for example, fatty acid polyglycol esters, may be used. In order to maintain the stability of plasmids, suitable substances having a selective action may be added to the medium. In order to maintain aerobic conditions, oxygen or gas mixtures containing oxygen, such as, for example, air, are introduced into the culture. The temperature of the culture is normally from 20° C. to 45° C. and preferably from 25° C. to 40° C. The culture is continued until the maximum amount of cysteine compounds has formed. That aim is normally achieved within a period of from 10 hours to 160 hours.

The fermentation liquors so obtained contain the cysteine compounds, that is to say one or more compounds selected from the group L-cysteine, L-cystine and thiazolidines, the biomass of the microorganism used, and the further non-cellular ingredients of the fermentation liquor, or secondary products.

The fermentation liquors usually have a content of total dry material of from 5 to 25 wt. %. The content of cysteine compounds is generally from 0.5 to 10 wt. % or from 1 to 10 wt. %. Higher contents are also possible. The content of biomass (expressed as dry material) is generally from 1 to 5 wt. %.

In order to produce a liquid form of the animal-feed additive according to the invention that is free of biomass, the biomass is removed completely (100%) from the resulting fermentation liquor by separation methods such as, for example, centrifugation, filtration, decantation, flocculation or a combination thereof. Such separation methods are known in the prior art and are described, for example, in the textbook of Belter et al. (Bioseparations, Downstream Processing for Biotechnology, John Wiley and Sons, Inc., 1988) or in Cooper (Ultrafiltration Membranes and Applications, Polymer Science and Technology Volume 13, Plenum Press, 1980). The resulting biomass-free liquor is then optionally thickened or concentrated by known methods, such as, for example, by means of a rotary evaporator, a thin-layer evaporator, a falling film evaporator, by reverse osmosis, or by nanofiltration.

The proportion of the individual components of the cysteine compounds, that is to say the proportion of L-cysteine, L-cystine and thiazolidines, in the liquid forms according to the invention of the animal-feed additives can be controlled by additional process steps.

If a high proportion of L-cystine is desired, an oxidizing agent, for example oxygen ($O_2$) or hydrogen peroxide ($H_2O_2$), is added to the fermentation liquor or is added during a working-up step. If a high content of L-cysteine is desired, L-cystine is reduced to L-cysteine by electrochemical processes such as are described in the prior art, for example in Ralph et al. (Journal of Electroanalytical Chemistry 375(1-2), 1-5 (1994) and 375(1-2) 17-27 (1994)) and in EP-A-0235908.

The L-cysteine that is formed or present can be stabilized by addition of reducing agents such as, for example, vitamin C (ascorbic acid), vitamin E (tocopherol) or formic acid or their salts. In order to stabilize the L-cysteine, individual working steps are optionally carried out with the exclusion of air or under a protecting gas atmosphere, for example nitrogen ($N_2$). In order to improve the solubility of the L-cystine, acidification can be carried out with an acid, for example a mineral acid such as sulfuric acid ($H_2SO_4$) or hydrochloric acid (HCl). The choice of the reducing or oxidizing agents and further auxiliary substances is so carried out that they are harmless in respect of the preparation and use of feed additives.

One or more of the cysteine compounds selected from the group L-cysteine, L-cystine and thiazolidines is optionally added in the form of the pure substance or a concentrate or in the form of preparations or mixtures containing them, the added amount of cysteine compound being such that the total concentration thereof, optionally including its salts, in the animal-feed additive is in the range from 1 to 98 wt. %.

In order to produce the solid forms of the animal-feed additives according to the invention, further water is removed from the described liquid forms. The solid forms are produced starting from variants of the liquid forms that are free of biomass or low in biomass or rich in biomass, as required, the liquid forms in that respect representing a precursor for the production of the solid forms of the animal-feed additives according to the invention.

The fermentation liquor free of biomass or low in biomass or rich in biomass is thickened or concentrated by known methods, such as, for example, by means of a rotary evaporator, a thin-layer evaporator, a falling film evaporator, by reverse osmosis, or by nanofiltration. The concentrated liquor is then worked up to a preferably pourable, finely divided powder by methods of lypophilisation, spray drying, spray granulation or by other processes. Such methods are described, for example, in the textbook of Blanch and Clark (Biochemical Engineering, Marcel Dekker Inc., New York, USA, 1997).

The invention also provides a process for the production of feed additives characterized in that it comprises producing a feed additive containing cysteine compounds from a thickened fermentation liquor that is free of biomass or low in biomass or rich in biomass by (c) one or more measures selected from the group drying, spray drying, spray granulation and granulation.

That pourable, finely divided powder can then in turn be converted into a coarse-grained, readily pourable, storable and largely dust-free product by suitable compacting or granulating processes. It is advantageous in the granulation or compacting to use conventional organic or inorganic auxiliary substances or carriers, such as starch, gelatin, cellulose derivatives or similar substances, as are conventionally employed in the processing of foodstuffs or feeds as binders, gelling agents or thickeners, or to use further substances such as, for example, silicas, silicates or stearates.

It is also possible for the product to be applied to an organic or inorganic carrier that is known and conventional in the processing of feeds, such as, for example, silicas, silicates, meals, brans, flours, starches, sugars, etc., and/or to be mixed and stabilized with conventional thickeners or binders. Application examples and processes therefor are described in the prior art, for example in Heidenreich and Löwe (Die Mühle+Mischfuttertechnik 132 (49), 817-820, (1995)).

Finally, the product can be brought into a state in which it is stable to digestion by animal stomachs, by coating processes using film-forming agents such as, for example, metal carbonates, silicas, silicates, alginates, stearates, starches, rubbers and cellulose ethers, as described in DE-C-4100920.

The proportion of the individual components of the cysteine compounds, that is to say the proportion of L-cysteine, L-cystine and thiazolidines, in the solid forms according to the invention of the animal-feed additives can be controlled by additional process steps.

If a high proportion of L-cystine is desired, an oxidizing agent, for example oxygen ($O_2$) or hydrogen peroxide ($H_2O_2$), is added to the fermentation liquor or is added during a working-up step. If a high content of L-cysteine is desired, L-cystine is reduced to L-cysteine by electrochemical processes such as are described in the prior art. The L-cysteine that is formed or present can be stabilized by addition of reducing agents such as, for example, vitamin C (ascorbic acid), vitamin E (tocopherol) or formic acid or their salts. In order to stabilize the L-cysteine, individual working steps are optionally carried out with the exclusion of air or under a protecting gas atmosphere, for example nitrogen ($N_2$). In order to improve the solubility of the L-cystine, acidification can be carried out with an acid, for example a mineral acid such as sulfuric acid ($H_2SO_4$). The choice of the reducing or oxidizing agents and further auxiliary substances is so carried out that they are harmless in respect of the preparation and use of feed additives.

One or more of the cysteine compounds selected from the group L-cysteine, L-cystine and thiazolidines is optionally added in the form of the pure substance or a concentrate or in the form of preparations or mixtures containing them, the added amount of cysteine compound being such that the total concentration thereof, optionally including its salts, in the animal-feed additive is in the range from 1 to 98 wt. %.

A further object of the invention comprises additionally carrying out one or more of the following steps in the above-described processes according to the invention:
  (i) electrochemical reduction (electrolysis) of the L-cystine to L-cysteine in one or more of the above-mentioned steps a) and b);
  (ii) acidification with a concentrated mineral acid in one or more of the above-mentioned steps a) and b);
  (iii) addition of a reducing agent to one or more of the above-mentioned steps a), b) and c);
  (iv) use of a protecting gas in one or more of the above-mentioned steps a), b) and c);
  (v) addition of an oxidizing agent to one or more of the above-mentioned steps a), b) and c);
  (vi) addition of one or more cysteine compounds selected from the group L-cysteine, L-cystine and thiazolidines to one or more of the above-mentioned steps a), b) and c), the added amount of cysteine compound being such that the total concentration thereof, optionally including its salts, in the animal-feed additive is in the range from 1 to 98 wt. %;
  (vii) addition of auxiliary substances to one or more of the above-mentioned steps a), b) and c), for stabilization and increasing the storability, selected from the group silicas, silicates, stearates, meals, brans, cereal flours, flours; silicas, silicates, starches and sugars; or
  (viii) conversion of the substances obtained according to c), i) to vii) into a form stable in the animal's stomach by coating with film-forming agents.

The analytical determination of the cysteine compounds and other sulfur-containing chemical compounds can be carried out as described in EP-A-0885962. According to that specification, analysis of the total cysteine is effected by the method of Gaitonde (Biochemical Journal 104, 627-633 (1967)), which determines free cysteine and cysteine bonded as thiazolidine. Cystine dissolved in semi-concentrated hydrochloric acid can be determined in the same manner under reducing conditions (dithiothreitol, DTT). Free SH groups can be determined by means of 5,5'-dithiobis-2-nitrobenzoic acid (DTNB), as in Lee (Biochemical and Biophysical Research Communications 213, (3), 837-844 (1995)).

Alternatively, free cysteine and cysteine liberated from the equilibrium reaction of the thiazolidines is converted by oxidation under mild conditions, for example with atmospheric oxygen or hydrogen peroxide (DE-A-3202295), into cystine, which can easily be determined automatically together with the cystine precipitated in the fermentation solution or present in the animal-feed additive. Any cysteic acid additionally formed can be determined and is to be taken into account.

Free cysteine and cysteine liberated from the equilibrium reaction of the thiazolidines, as well as precipitated and/or dissolved cystine, is preferably oxidized to cysteic acid by means of per-formic acid and determined by means of HPLC or amino acid analyzer according to the prior art, as described in Varga-Visi et al. (Chromatographia 2000, 51 Suppl., 325-327).

Methods of determining L-amino acids are known from the prior art. The analysis of L-cystine and/or L-cysteic acid can be carried out by ion-exchange chromatography with subsequent ninhydrin derivation, as described in Spackman et al. (Analytical Chemistry, 30, (1958), 1190-1206).

The present invention is explained in greater detail below by means of Embodiment Examples.

EXAMPLE 1

Preparation of the L-cysteine Production Strain W3110/pMW218cysE767ydeDrbs 1.1 Construction of Plasmid pMW218ydeDrbs Using the polymerase chain reaction (PCR) and synthetic oligonucleotides, the ydeD gene from E. coli K12 MG1655 is amplified so that an artificial ribosome binding site (RBS) is inserted upstream of the gene.

Starting from the nucleotide sequence of the ydeD gene in E. coli K12 MG1655 (Accession Number AE000339, Blattner et al. (Science 277, 1453-1474 (1997)), PCR primers are synthesized (MWG Biotech, Ebersberg, Germany). The 5' ends of the primers are lengthened with recognition sequences for restriction enzymes and six additional bases. For the ydeD-r1 primer, the recognition sequence for NcoI with an inserted artificial ribosome binding site (RBS) (double underlined) is chosen, and for the ydeD-2 primer, the recognition sequence for EcoRI is chosen, which are labeled in the nucleotide sequence shown below by simple underlining:

```
ydeD-r1 (SEQ ID No. 1):  5'-GATCTACCATGGAAAGGAGGACAACCATGAAATTCAGAGGCGGTAGAATGydeD-2  (SEQ ID No. 2):  5'-GATCTAGAATTCGTAGTTTGTTCTGGCCCCGACATCT-3'
```

The chromosomal E. coli K12 MG1655 DNA used for the PCR is isolated using "QIAGEN Genomic-tips 100/G" (QIAGEN, Hilden, Germany) in accordance with the manufacturer's instructions. A DNA fragment about 1000 base pairs (bp) in size can be amplified with the specific primers under standard PCR conditions (Innis et al. (1990) PCR Protocols. A Guide to Methods and Applications, Academic Press) with Vent-DNA polymerase (New England Biolabs, Frankfurt, Germany).

The PCR product is cleaved with the enzymes NcoI and EcoRI and ligated with plasmid pTrc99A (Pharmacia Biotech, Uppsala, Sweden), which has likewise been digested.

The E. coli strain DH5α is transformed with the ligation batch, and plasmid-carrying cells are selected on LB agar (Lennox, Virology 1:190 (1955)) to which 50 μg/ml ampicillin have been added.

The successful cloning of the ydeDrbs gene can be demonstrated after the plasmid DNA isolation and control cleavage with NcoI/EcoRI, SspI and ClaI. The plasmid is designated pTrc-ydeDrbs.

Starting from that plasmid, a PCR primer having an integrated BamHI cleavage site (underlined) is generated, which binds upstream of the Trc promoter:

```
ydeD-exp1 (SEQ ID No. 3):
5'-GATCTGGATCCGCCGACATCATAACGGTTCTGG-3'
```

For the construction of an expression plasmid, the ydeDrbs gene, including the Trc promoter, is amplified under standard PCR conditions (see above) with the primer pair ydeD-exp1 and ydeD-2 and plasmid DNA pTrc-ydeDrbs as template. The DNA fragment about 1100 bp in size is cleaved with the enzymes BamHI and EcoRI and ligated into the vector pMW218 (Nippon Gene, Toyama, Japan), which has likewise been digested. E. coli strain XL1-Blue MRF' (Stratagene, La Jolla, USA) is transformed with the ligation batch, and plasmid-carrying cells are selected on LB agar (Lennox, Virology 1:190 (1955)), to which 50 μg/ml kanamycin has been added. The successful cloning of the Trc-ydeDrbs fragment can be demonstrated after the plasmid DNA isolation and control cleavage with BamHI/EcoRI and BamHI/HindIII. The plasmid is designated pMW218ydeDrbs.

1.2 Construction of Plasmid pMW218cysE767ydeDrbs

The cysE767 gene from E. coli JM240/33, which, owing to a base substitution at position 767, has feedback resistance in respect of L-cysteine (Denk and Bock, Journal of General Microbiology 1987, 133:515-525), is amplified with synthetic oligonucleotides, using the PCR, so that the resulting DNA fragment contains the cysE767 gene and a region comprising the upstream, endogenous promoter. Strain E. coli JM240/33 is generally available under the designation CGSC Number 7914 from the E. coli Genetic Stock Center (830 Kline Biology Tower; MCD Biology Department; 266 Whitney Ave. Box 208103; Yale University; New Haven, Conn. 06520-8103).

Starting from the nucleotide sequence of the cysE gene in E. coli K12 MG1655 (Accession Number AE000339, Blattner et al. (Science 277, 1453-1474 (1997)), PCR primers with an inserted HindIII or BamHI cleavage site (underlined) are synthesized (MWG Biotech, Ebersberg, Germany):

```
cysE-ex1 (SEQ ID No. 4):
5'-GATCTAGAATTCAAGCTTGGCTACCGCAATACGAAAGAAG-3' cysE33-ex4 (SEQ ID No. 5):
5'-GATCTAGGATCCGGCACGATCACAGGACATTAGA-3'
```

The chromosomal E. coli JM 240/33 (Denk and Böck, Journal of General Microbiology 1987, 133:515-525) DNA used for the PCR is isolated using "QIAGEN Genomic-tips 100/G" (QIAGEN, Hilden, Germany) according to the manufacturer's instructions. A DNA fragment about 1110 base pairs (bp) in size can be amplified with the specific primers under standard PCR conditions (Innis et al. (1990) PCR Protocols. A Guide to Methods and Applications, Academic Press) with Vent-DNA polymerase (New England Biolabs, Frankfurt, Germany).

The PCR product is cleaved with the enzymes HindIII and BamHI and ligated with plasmid pMW218ydeDrbs from Example 1, which has likewise been digested.

E. coli strain XL1-Blue MRF' (Stratagene, La Jolla, USA) is transformed with the ligation batch, and plasmid-carrying cells are selected on LB agar (Lennox, Virology 1:190 (1955)), to which 50 μg/ml kanamycin has been added.

Figure 1:
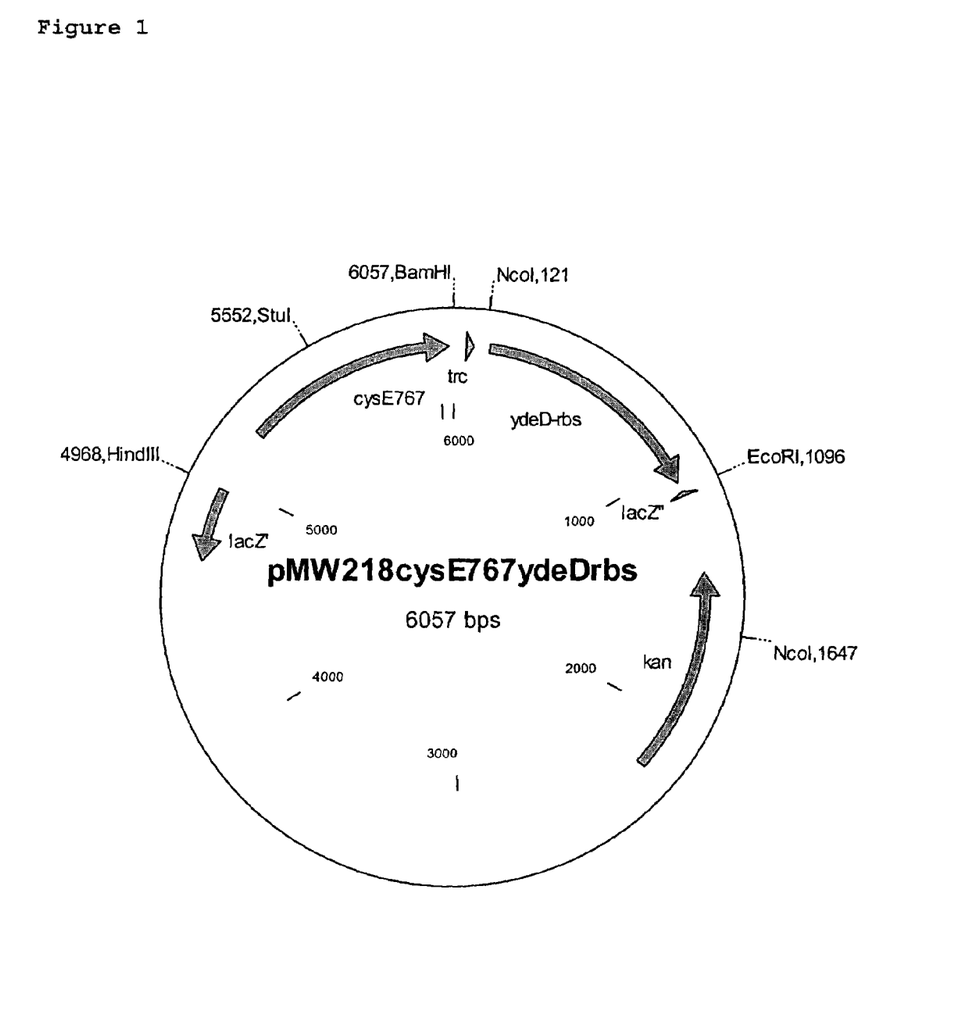

The successful cloning of the cysE767 gene can be demonstrated after the plasmid DNA isolation and control cleavage with HindIII/BamHI and HindIII/StuI. The plasmid is designated pMW218cysE767ydeDrbs (FIG. 1).

1.3 Production of Strain W3110/pMW218cysE767ydeDrbs

The E. coli wild-type strain W3110 is transformed with the plasmid pMW218cysE767ydeDrbs, and plasmid-carrying cells are selected on LB agar supplemented with 50 μg/ml kanamycin. The successful transformation of the plasmid pMW218cysE767ydeDrbs can be demonstrated after the plasmid DNA isolation and control cleavage with HindIII/BamHI.

The strain is designated W3110/pMW218cysE767ydeDrbs.

EXAMPLE 2

Production of L-cysteine, L-cystine and Thiazolidines by Fermentation with the Aid of Escherichia coli Strain W3110/pMW218cysE767ydeDrbs Cells were rinsed off an agar plate using LB medium. 10 μl of the rinsed-off material were added to 10 ml of LB medium plus 20 mg/l kanamycin. That starting culture was incubated overnight at 30° C. The first pre-culture was carried out in a shaking flask and inoculated 1:100 (2.5 ml) from the starting culture. To that end, shaking flasks having a volume of 1l were charged with LB medium, and the latter was supplemented with 20 mg/l kanamycin. Four shaking flasks each having a filling volume of 250 ml were incubated at a shaking frequency of 125 revolutions per minute and a temperature of 30° C. to an $OD_{660}$ of 2.4. The contents of the four flasks were then purified and served as inoculum for the second pre-culture.

A volume of 1l of that first pre-culture was inoculated in 5000 g of nutrient medium A1-179. The culture fermentation (second pre-culture) was carried out in 10 l stirred-reactor fermenters from B. Braun (BBI, Germany, Melsungen, model Biostat ED). Nutrient medium A1-179 contained the constituents listed in Table 1. That second pre-culture was cultivated for 17 hours at a temperature of 30° C., with volume-specific gassing of 0.6 vvm (volume per volume per minute), at an oxygen partial pressure of 20% of air saturation and a pH of pH 7.0 until an $OD_{660}$ of 3.4 was reached.

For the inoculation of 15 kg of growth medium M1-708, which was contained in 40 l stirred-reactor fermenters LP42 from Bioengineering (Wald, Switzerland), 1500 g of the second pre-culture in nutrient medium A1-179 were added. The growth medium M1-708 contained the constituents listed in Table 2. The culture was cultivated for 6 hours at a temperature of 30° C., an aeration of 22.5/min. (liters per minute), a minimal stirring of 200 rpm and a pH of 7.0 and an oxygen partial pressure of 50% of air saturation, until the sugar introduced had been consumed completely. The liquor so obtained was then cultivated for a further 90 hours at a temperature of 30° C., an oxygen partial pressure of 50% of air saturation and a pH value of pH 7.0, until an OD660 of 78.8 was reached. During that time, 8804 g of a production medium consisting of a starch hydrolysate solution having a concentration of 560 g/l glucose were fed in continuously. The glucose concentration in the fermenter was established at between 5 and 20 g/l. 3036 g of a sodium thiosulfate solution having a concentration of 900 g/kg were also fed in continuously.

The optical density (OD) was measured using a digital photometer of the LP1W type from Dr. Bruno Lange GmbH (Berlin, Germany) at a measuring wavelength of 660 nm. The optical density of the fermentation end sample was 78.9.

The concentration of L-cysteine and L-cystine was determined using an amino acid analyzer from Biochrom (Cambridge, UK) by ion-exchange chromatography and post-column reaction with ninhydrin detection. Alternatively or additionally, photometric measurement of the total cysteine (L-cysteine, L-cystine and thiazolidines) was carried out by the method of Gaitonde using a photometer of the Uvicon 933 type from Kontron (Germany). The approximate content of thiazolidines was estimated by subtracting the sum of the content of L-cysteine and L-cystine (as cysteine equivalent) from the total cysteine content according to Gaitonde.

An L-cysteine concentration of 2.5 g/kg was determined in the fermentation end sample after 96 hours. The concentration of L-cystine was 5.8 g/kg. The concentration of thiazolidines was estimated at 0.6 g/kg. The content of total dry mass was 8.76 wt. % (percent by weight).

TABLE 1

| Component | Concentration (per kg) |
| --- | --- |
| Composition of nutrient medium A1-179 | |
| Glucosse H2O | 5.4 g |
| $K_2HO_4$ | 11.76 g |
| $KHPO_4$ | 2.94 g |
| $(NH_4)SO_4$ | 4.9 g |
| $MgSO_4 \cdot 7H_2O$ | 0.29 g |
| $CaCl2 \cdot 2H_2O$ | 0.01 g |
| NaCL | 0.1 g |
| $FeSO_4 \cdot 7H_2O$ | 2 mg |
| Sodium citrate | 0.98 g |
| Thiamin HCl | 5 mg |
| Kanamycin | 20 mg |
| Trace element solutions | 1 g |
| Composition of the trace elements solution for nutrient medium A1-179 and M1-708 | |
| $Na_2MoO_4 \cdot 2H_2O$ | 0.15 g |
| $H_3BO_3$ | 2.5 g |
| $CoCl_2 \cdot 6H_2O$ | 0.7 g |
| $CuSO_4 \cdot 5H_2O$ | 0.25 g |
| $MnCl_2 \cdot 4H_2O$ | 1.6 g |
| $ZnSO_4 \cdot 5H_2O$ | 0.3 g |

TABLE 2

| Component | Concentration (per kg) |
| --- | --- |
| Composition of growth medium M1-708 | |
| Glucose $H_2O$ | 16.33 g |
| Yeast extract | 4.9 g |
| Trypton | 9.8 g |
| NaCl | 0.49 g |
| $(NH_4)_2SO_4$ | 4.9 g |
| $KH_2PO_4$ | 1.47 g |
| $MgSO_4 \cdot 7H_2O$ | 0.294 g |
| $CaCl_2 \cdot 2H_2O$ | 0.015 g |
| $FeSO_4 \cdot 7H_2O$ | 74 mg |
| Sodium citrate | 0.98 g |
| Thiamin HCl | 5 mg |
| Kanamycin | 20 mg |

TABLE 2-continued

| Component | Concentration (per kg) |
| --- | --- |
| Composition of growth medium M1-708 | |
| Trace element solution | 1 g |

EXAMPLE 3

Production of a Liquid Product Containing 100% of the Biomass Formed During the Fermentation 3052 g of the fermentation liquor from Example 2 were thickened to 526 g in five hours in a RE-120 rotary evaporator from Büchi (Büchi Labortechnik, Flawil, Switzerland) at 60° C., a pressure of 30-40 mbar and a speed of rotation of 30 revolutions per minute.

An L-cysteine concentration of 11.4 g/kg was determined in the resulting product. The concentration of L-cystine was 18.0 g/kg. The content of total dry mass was 50.1 wt. %.

EXAMPLE 4

Production of a Liquid Product Free of Biomass (0% Biomass) Using Hydrochloric Acid (HCl)

2500 g of the fermentation liquor from Example 2 were adjusted to 0.5 M HCl with 105 ml of 37% HCl and stirred for 10 minutes. The biomass was then made to settle out for 20 minutes in a centrifuge (Heraeus Biofuge Stratos, Heraeus, Germany) at 3500 revolutions per minute and at room temperature. 2180 g of the clear supernatant were then thickened to 336 g in five hours in a RE-120 rotary evaporator from Büchi (Büchi Labortechnik, Flawil, Switzerland) at 60° C., a pressure of 20-30 mbar and a speed of rotation of 30 revolutions per minute.

Traces of L-cysteine were detected in the resulting product. The concentration of L-cystine was 44.5 g/kg. The concentration of thiazolidines was estimated at 28 g/kg. The content of total dry mass was 50.9 wt. %.

EXAMPLE 5

Production of a Liquid Product Containing 50% of the Biomass Formed During the Fermentation and 50% Dry Mass Fermentation liquor from Example 2 was centrifuged for 20 minutes in a centrifuge (Heraeus Biofuge Stratos, Heraeus, Germany) at 3500 revolutions per minute and at room temperature. 1317 g each of the centrifuged liquor and the original fermentation liquor were mixed. The resulting 2634 g were then dried to 400 g in 4.5 hours in a RE-120 rotary evaporator from Büchi (Büchi Labortechnik, Flawil, Switzerland) at 50-60° C., a pressure of 30-40 mbar and a speed of rotation of 30 revolutions per minute.

An L-cysteine concentration of 13.2 g/kg was determined in the resulting product. The concentration of L-cystine was 9.7 g/kg. The concentration of thiazolidines was estimated at 26 g/kg. The content of total dry mass was 49.7 wt. %.

EXAMPLE 6

Production of a Liquid Product Containing about 33% of the Biomass Formed During the Fermentation 9310 g of fermentation liquor from Example 2 were filtered in a filtration installation from Rhodia (Rhodia Minicarbosep, Emmenbrücke, Switzerland). The filtration installation was equipped with a membrane manufactured by Tami (0.45 µm, Tami, Hermsdorf, Germany), so that the biomass remained in the retained material. After 450 minutes' filtration, 6970 g of filtrate were present. 2005 g of that filtrate were mixed with 1002 g of the fermentation liquor. The resulting 3007 g were then thickened to 414 g in 4.3 hours in a RE-120 rotary evaporator from Büchi (Büchi Labortechnik, Flawil, Switzerland) at 50-60° C., a pressure of 30-40 mbar and a speed of rotation of 30 revolutions per minute.

An L-cysteine concentration of 11.8 g/kg was determined in the resulting product. The concentration of L-cystine was 9.7 g/kg. The concentration of thiazolidines was estimated at 27 g/kg. The content of total dry mass was 48.9 wt. %.

EXAMPLE 7

Production of a Liquid Product Free of Biomass (0% Biomass)

9310 g of fermentation liquor from Example 2 were filtered in a filtration installation from Rhodia (Rhodia Minicarbosep, Emmenbrücke, Switzerland). The filtration installation was equipped with a membrane manufactured by Tami (0.45 µm, Tami, Hermsdorf, Germany), so that the biomass remained in the retained material. After 450 minutes' filtration, 6970 g of filtrate were present. 3200 g of the clear supernatant were then thickened to 358 g in five hours in a RE-120 rotary evaporator from Büchi (Büchi Labortechnik, Flawil, Switzerland) at 60° C., a pressure of 20-30 mbar and a speed of rotation of 30 revolutions per minute.

An L-cysteine concentration of 10.9 g/l was determined in the resulting product. The concentration of L-cystine was 6.8 g/l. The concentration of thiazolidines was estimated at 26 g/kg. The content of total dry mass was 46.34 wt. %.

EXAMPLE 8

Production of a Solid Product Containing 100% of the Biomass Formed During the Fermentation 735 g of fermentation liquor from Example 2 were dried in a B190 spray drier from Büchi (Büchi Labortechnik, Flawil, Switzerland). The temperature on entry into the spray tower was 115° C., the discharge temperature was 76° C. and the pressure was 50 mbar. 54.6 g of product were obtained.

An L-cysteine concentration of 24.7 g/kg was determined in the resulting product. The concentration of L-cystine was 17.1 g/kg. The concentration of thiazolidines was estimated at 50 g/kg.

EXAMPLE 9

Production of a Solid Product Containing 33% of the Biomass Formed During the Fermentation 9310 g of fermentation liquor from Example 2 were filtered in a filtration installation from Rhodia (Rhodia Minicarbosep, Emmenbrücke, Switzerland). The filtration installation was equipped with a membrane manufactured by Tami (0.45 µm, Tami, Hermsdorf, Germany), so that the biomass remained in the retained material. After 450 minutes' filtration, 6970 g of filtrate were present. 404.9 g of the filtrate were mixed with 202.1 g of fermentation liquor. The 607 g of resulting mixture were dried in a B190 spray drier from Büchi (Büchi Labortechnik, Flawil, Switzerland). The temperature on entry into the spray tower was 118° C., the discharge temperature was 80° C. and the pressure was 45 mbar. 34.1 g of product were obtained.

An L-cysteine concentration of 17.8 g/kg was determined in the resulting product. The concentration of L-cystine was 14.9 g/kg. The concentration of thiazolidines was estimated at 16 g/kg.

EXAMPLE 10

Production of a Solid Product Containing 50% of the Biomass Formed During the Fermentation 9310 g of fermentation liquor from Example 2 were filtered in a filtration installation from Rhodia (Rhodia Minicarbosep, Emmenbrücke, Switzerland). The filtration installation was equipped with a membrane manufactured by Tami (0.45 µm, Tami, Hermsdorf, Germany), so that the biomass remained in the retained material. After 450 minutes' filtration, 6970 g of filtrate were present. 350 g of the filtrate were mixed with 350 g of fermentation liquor. The 700 g of resulting mixture were dried in a B190 spray drier from Büchi (Büchi Labortechnik, Flawil, Switzerland). The temperature on entry into the spray tower was 116° C., the discharge temperature was 76° C. and the pressure was 50 mbar. 38.7 g of product were obtained.

An L-cysteine concentration of 21.0 g/kg was determined in the resulting product. The concentration of L-cystine was 14.8 g/kg. The concentration of thiazolidines was estimated at 26 g/kg.

EXAMPLE 11

Production of a Solid Product Free of Biomass (0% biomass)

9310 g of fermentation liquor from Example 2 were filtered in a filtration installation from Rhodia (Rhodia Minicarbosep, Emmenbrücke, Switzerland). The filtration installation was equipped with a membrane manufactured by Tami (0.45 µm, Tami, Hermsdorf, Germany), so that the biomass remained in the retained material. After 450 minutes' filtration, 6970 g of filtrate were present. 602 g of filtrate were dried in a B190 spray drier from Büchi (Büchi Labortechnik, Flawil, Switzerland). The temperature on entry into the spray tower was 116° C., the discharge temperature was 76° C. and the pressure was 50 mbar. 21 g of product were obtained.

An L-cysteine concentration of 15.7 g/kg was determined in the resulting product. The concentration of L-cystine was 10.2 g/kg. The concentration of thiazolidines was estimated at 10 g/kg.

EXAMPLE 12

Production of a Solid Product Free of Biomass (0% Biomass), Containing Sipernat 2200

An aliquot of the fermentation liquor from Example 2 was adjusted to 0.5 M HCl with 37% HCl. The biomass was then made to settle out for 20 minutes in a centrifuge (Heraeus Biofuge Stratos, Heraeus, Germany) at 3500 revolutions per minute and at room temperature. About 600 ml of the clear supernatant were then thickened to 94 g in five hours in a RE-120 rotary evaporator from Büchi (Büchi Labortechnik, Flawil, Switzerland) at 60° C., a pressure of 20-30 mbar and a speed of rotation of 30 revolutions per minute. The 94 g of residue were mixed with 30 g of silica of the Sipernat 2200 type (Degussa, Düsseldorf, Germany) and dried at 60-70° C.

No L-cysteine could be detected in the resulting product. The concentration of L-cystine was 44.9 g/kg.

BRIEF DESCRIPTION OF THE FIGURE

FIG. 1: Map of plasmid pMW218cysE767ydeDrbs containing the cysE767 and the ydeDrbs gene The indicated numbers of base pairs (bps) are approximate values obtained within the scope of the reproducibility of measurements. The abbreviations and designations used have the following meanings:

lacZ": 5' region of the alpha gene fragment of the lacZ gene lacZ': 3' region of the alpha gene fragment of the lacZ gene Kan: kanamycin resistance gene trc: trc promoter of plasmid pTrc99A cysE767: cysE gene fragment from *E. coli* strain JM240/33 ydeD-rbs: ydeD gene with artificial ribosome binding site

The abbreviations for the restriction enzymes have the following meanings

BamHI: restriction endonuclease from *Bacillus amyloliquefaciens* H

EcoRI: restriction endonuclease from *E. coli*

HinDIII: restriction endonuclease from *Haemophilus influenzae* Rd

NcoI: restriction endonuclease from *Nocardia corallina*

StuI: restriction endonuclease from *Streptomyces tubercidicus*

What is claimed is:

1. An animal-feed additive based on a fermentation liquor, comprising:
   a) one or more cysteine compounds selected from the group consisting of L-cysteine, L-cystine, thiazolidines, and salts thereof, and
   b) from 2% to 100% of other non-cellular ingredients of the fermentation liquor.

2. An animal-feed additive based on a fermentation liquor, comprising:
   a) a thiazolidine or a combination of a thiazolidine together with at least one of L-cysteine, L-cystine, and salts thereof, and
   b) from 2% to 100% of other non-cellular ingredients of the fermentation liquor.

3. The animal-feed additive according to claim 1 or 2, wherein the thiazolidine is one or more compounds selected from the group consisting of 2-methyl-thiazolidine-2,4-dicarboxylic acid, 2-carboxymethyl-thiazolidine- 2,4-dicarboxylic acid, 2-carboxyethyl-thiazolidine-2,4-dicarboxylic acid, and thiazolidine-2,4- dicarboxylic acid.

4. The animal-feed additive according to claim 1 or 2, wherein the salt of the cysteine compound is one or more salts selected from the group consisting of the sodium, potassium, ammonium, magnesium and calcium salt.

5. The animal-feed additive according to claim 1, wherein the fermentation liquor contains a biomass in an amount ranging from >2% to ≦50% in the animal-feed additive.

6. The animal-feed additive according to claim 1, wherein the fermentation liquor contains a biomass in an amount ranging from >50% to 100% in the animal-feed additive.

7. The animal-feed additive according to claim 1, wherein said cysteine compound or salt thereof is present in the feed in an amount ranging from 1 to 98 wt.%.

8. The animal-feed additive according to claim 1 or 2, which further comprises one or more chemical compounds selected from the group consisting of glutathione, cystathionine, biotin, thiamin, liponic acid, coenzyme A and L-methionine.

9. The animal-feed additive according to claim 1, which is in liquid form.

10. The animal-feed additive according to claim 1 which is in solid form.

* * * * *